United States Patent [19]

Schneider et al.

[11] 4,106,219
[45] Aug. 15, 1978

[54] PLASTIC BONE USED FOR TRAINING PURPOSES BY SURGEONS

[75] Inventors: Urs Schneider, Kronbühl; Rudolf Heller, Zurich, both of Switzerland

[73] Assignees: Synthes AG Chur, Chur; Contraves AG, Zurich, both of Switzerland

[21] Appl. No.: 743,393

[22] Filed: Nov. 19, 1976

[30] Foreign Application Priority Data

Dec. 5, 1975 [CH] Switzerland .................. 15841/75

[51] Int. Cl.² .............................................. G09B 23/32
[52] U.S. Cl. .......................................................... 35/17
[58] Field of Search ............................................. 35/17

[56] References Cited
U.S. PATENT DOCUMENTS

| | | | |
|---|---|---|---|
| 1,882,575 | 10/1932 | Hanks | 35/17 UX |
| 2,988,823 | 6/1961 | Rosenbloom | 35/17 |
| 2,995,833 | 8/1961 | Bezark | 35/17 |
| 3,895,451 | 7/1975 | Smrcka | 35/17 |

Primary Examiner—Harland S. Skogquist
Attorney, Agent, or Firm—Werner W. Kellman

[57] ABSTRACT

A plastic bone used as a training device or teaching aid for a surgeon for mechanically connecting bone fractures, comprising a plastic molded part, the size and dimension of which approximates that of a human extremity-shaft bone having an internal hollow compartment or cavity which extends past a marrow cavity region at the center of the shaft towards both shaft ends into the region of the spongy structured bone lacunae (spongiosa) and widens. The wall structure of the bone approximately corresponds to the solid or compact wall parts (compacta) of the natural structure in weight, strength and mechanical workability.

4 Claims, 2 Drawing Figures

PLASTIC BONE USED FOR TRAINING PURPOSES BY SURGEONS

BACKGROUND OF THE INVENTION

The present invention relates to a new and improved construction of a plastic bone serving as a training device or teaching aid for surgeons or other medical personnel for mechanically connecting bone fractures.

For the surgical treatment of bone fractures the reader is directed to the state of the art publication entitled "Manual der Osteosynthese", by M. E. Muller, M. Allgower, H. Willenegger, Springer Publishers, Berlin, Heidelberg, N.Y. 1969. In this text there has been explained, on the basis of numerous illustrations and descriptive material, the technical aids and techniques available to the orthopedic surgeon for treating complicated fractures and shattering of the bones, especially at the extremities, in order to enable the patient to again reuse the injured bone after a relatively short period of time and thereafter to render possible complete healing of the damaged limb. These treatment techniques and especially the mechanical-technical proper use of the available aids i.e. fracture appliances or the like, require the surgeon to participate in intensive training courses in orthopedic surgery to avoid making mistakes in practice, and further, requires practical experience with mechanical connection techniques employed at bones used for training or teaching purposes.

The training bones heretofore available primarily were animal bones procured from slaughter houses, and in rare situations also human bones. The available animal bones, especially with respect to their internal and external structure, but also with regard to their strength, considerably deviated from analogous human bones. Human bones were only used for training purposes with reservation because of ethical reasons. Additionally, oftentimes they only first could be used after undergoing a longer preservation period and pre-treatment, during the course of which their strength, fracture behavior and mechanical working properties frequently disadvantageously changed in relation to the corresponding properties of the living bone.

Plastic bones heretofore were only known as a toy and chewing or gnawing bone for dogs, for demonstrating the external bone shape, or for assembling a demonstration skeleton. In all these cases there was not provided any marrow cavity, and significantly, the internal structure did not have to correspond in any manner to the natural bone structure.

In U.S. Pat. No. 2,472,819 there have been taught, for instance, bone models and entire limb-skeleton models formed of wood, which extensively correspond in their external shape to the actual human bones. They provide a certain training help for the student of anatomy and surgery in order to properly set fractures and to orient the individual bones in the sockets.

Owing to the extreme differences between a solid natural wooden structure and a bone structure having a marrow cavity, bone lacunae and compact outer shell or layer, it is not possible however to use the same tools for the connection of the fractured parts and not the same fracture setting or orthopedic appliances (screws, etc.).

SUMMARY OF THE INVENTION

It is a general object of the present invention to provide an improved plastic bone useful as a training device for surgeons or other medical personnel, such as medical students.

Another and more specific object of the present invention aims at providing plastic bones suitable as a training aid for surgeons or the like for the mechanical connection of fractures, preferably plastic bones in the form of human extremity-shaft bones, at which there can be practiced in a manner extensively similar to conditions arising in practice the heretofore mentioned techniques for the continuous, rigid connection of bone fractures with marrow nails driven into the appropriately drilled marrow cavity and/or with externally threadably connected holding plates or other fracture connection appliances or elements.

Another object of the present invention aims at the provision of plastic bones of the previously mentioned character which with respect to their external shape, the shape of their inner hollow compartment or cavity, as well as also with regard to their outer wall structure correspond with sufficient accurate approximation to the outer, compact wall parts of the natural structure in respect to strength, fracture behavior and mechanical workability or machinability.

It is another object of the present invention to devise a plastic bone wherein importantly the employed plastic material can be machined equally as well as the natural bone substance by means of tools, such as drilling- and thread cutting tools used in orthopedic surgery.

Many types of conventional plastic materials, such as for instance thermoplastic or high-strength plastics reinforced with glass fibers, during drilling and thread cutting of the employed material tend to bind, and thus, considerably render more difficult the corresponding machining work.

Now in order to implement the foregoing objects and still further objects of the invention, which will become more readily apparent as the description proceeds, the plastic bone of the present invention is manifested by the features that it is constructed as a cast or molded plastic element which in shape and size corresponds to a human extremity-shaft bone having an inner compartment or cavity which extends past a narrow marrow cavity region at the shaft center towards both shaft ends at the region of more markedly formed bone lucanae (spongiosa) of the natural structure and widens, and the wall structure of which approximately corresponds to the compact or solid wall parts (compacta) of the natural structure with respect to weight, strength and mechanical machinability.

The plastic bone of the invention is preferably constructed as a one-piece rigid polyurethane foam casting with practically unfoamed boundary layers and a microcellular structured intermediate layer of its wall.

Advantageously, the inner compartment or cavity at the region of the intermediate shaft portion has a uniform narrow and profiled cross-section which possesses recesses between inwardly protruding ribs and/or pins, for the reception of chips formed when drilling to a predetermined inner diameter.

Furthermore, depending upon the specific desires, at least this widening or enlargement of the inner cavity or compartment at the region of the head ends can be filled with a particularly light foam-support or reinforcing material which, in turn, can be imbued with a lubricant in order to still better simulate the conditions arising during actual drilling of the marrow cavity.

Because a core insert for forming the inner hollow cavity or compartment of the described type cannot be removed in another manner from the casting mold after hardening of the wall structure, unless the plastic bone is fabricated of two longitudinal halves or parts which are subsequently adhesively bonded to one another, it is thus advantageous to cast the core insert in an appropriate casting mold in a conventional manner from a material having a melting point in the range of about 50° C to 100° C, composed of a wax or a suitable metal alloy, for instance, Wood's alloy, Rose's metal, "bismuth solder" for "bismuth cadmium-solder". Such core insert-cast parts, after hardening of the cast or molded bone, can be melted by heating the mold and emptied through a discharge hole.

Also it would be possible to fabricate the core insert from a material which, after hardening of the plastic bone, can be physically or chemically dissolved out of the internal compartment with the aid of water or another solvent. A further possibility is to fabricate the shape-imparting core insert from a support or reinforcing material which can remain in the internal cavity or compartment of the finished plastic bone without any significant drawback.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figures 1, 2:
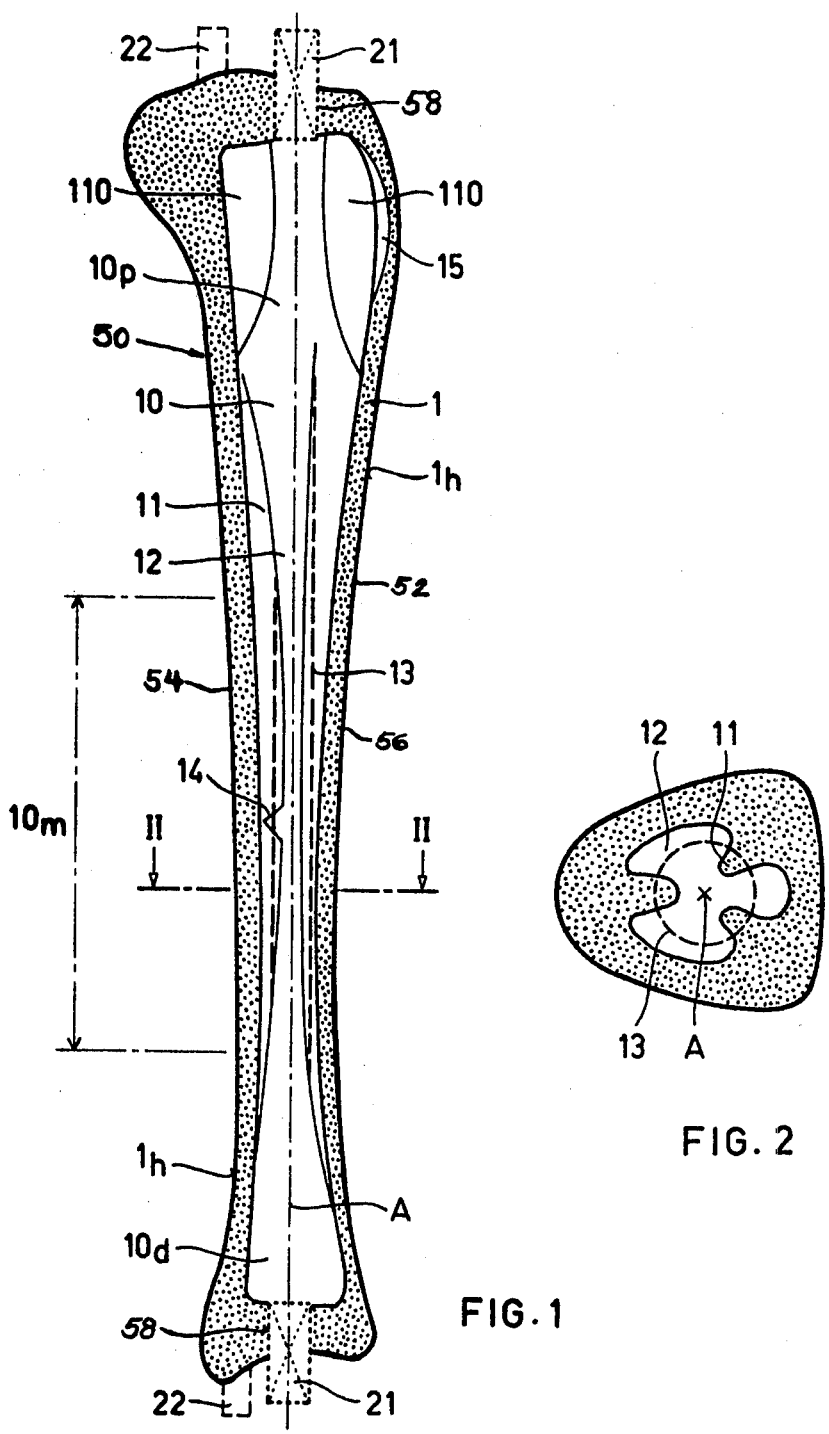
FIG. 1 is a longitudinal sectional view of a plastic bone constructed according to the present invention.
FIG. 2 is a cross-sectional view of the bone shown in FIG. 1, taken substantially along the line II-II thereof.

Describing now the drawings, the plastic bone 50 illustrated by way of example therein, preferably is constructed as a rigid polyurethane foam cast or molded product, hereinafter simply conveniently referred to as a molded part or product. Its external shape and its inner cavity 10 essentially corresponds to the tibia of the shin-bone or shank of a human. At the central portion or region $10_m$ of the bone shaft 52 its internal cavity or compartment 10 possesses the narrowest cross-section and at this region has an approximately uniform cross-section and corresponds essentially to the marrow cavity of the natural bone. At this narrowest central region or section $10_m$ the inner cavity 10 is profiled and, according to the showing of FIG. 2, forms recesses 12 between inwardly protruding ribs or protuberances 11. The recesses 12 serve to receive the chips or the like produced during drilling to a predetermined cylinder diameter for the fixation of a marrow nail or equivalent structure which is to be driven-in. This hollow marrow cavity $10_m$ can be drilled, for instance, approximately to the shape of a cylinder according to the circle 13 shown in phantom lines in FIG. 2, where the marrow nail which is to be driven-in must be fixedly seated along a length of about 10 to 15 centimeters in order to ensure for the mutual fixation of the bone parts in the case of a central shaft fracture.

From this profiled marrow cavity — central portion $10_m$ the inner cavity or compartment 10 widens towards the proximal head end and towards the distal head end of the entire plastic bone, i.e. into the region of the spongy bone tissue of the natural structure (spongiosa region). These widened upper and lower end portions of the inner cavity 10 are designated by reference character $10_p$ (proximal end) and reference character $10_d$ (distal end) and can be left empty without any disadvantage for the contemplated field of use. However, if the user so desires for certain reasons of use, then the entire inner cavity 10 or also only its widened end portions $10_p$ and $10_d$ can be filled with a foamable reaction mixture by means of auxiliary bore holes after for instance hardening of the bone body, this reaction mixture setting to form a light foam structure, for instance a coarse cell structure which, for instance, also can be imbued with a lubricant.

The wall 1 enclosing the inner cavity 10 of the illustrated plastic bone 50 advantageously consists of a rigid polyurethane foam structure molded in a multi-part closed mold containing a mold core inserted therein and hardened in the closed mold. At the region of the proximal widened portion or end $10_p$ of the inner cavity 10 the wall 1 can be laterally compacted and provided with inner ribs and/or plugs 110 which afford support for an angle plate which is to be driven-in, similar to the support provided by the spongy bone tissue present in the natural bone structure. As mentioned, the bone 50 can be formed of two longitudinal molded halves 54, 56, suitably interconnected with one another.

An example of a rigid polyurethane foam reaction mixture suitable for manufacturing the inventive plastic- or training bone is a liquid mixture consisting of:

100 parts by weight polyol, e.g. "DESMOPHEN B 641" a registered trademark of the well known German firm Bayer Leverkusen, i.e. polyesters and/or polyethers including at least two reactive hydroxyl groups;

100 parts by weight higher functional isocyanate, e.g. "DESMODUR 44 V 10", also a registered trademark of Bayer Leverkusen, a liquid containing polyisocyanates free of solvents and containing one or more diisocyanates such as diphenyl methane - 4,4'-diisocyanate; and 5 parts by weight propellent, e.g. "Frigen 11" (trichloromonofluoromethane), a registered trademark of Dupont.

This rigid polyurethane foam reaction mixture begins to foam at room temperature approximately after 15 seconds and subsequently begins to set. It is advantageous to use metal both for the outer mold as well as also for the core and prior to the injection of the reaction mixture to cool at least the outer mold to relatively lower temperatures (15° C to 20° C) so that the reaction mixture layers bearing at this mold or core surfaces cool and are thus prevented from foaming. Hence, after hardening there are formed unfoamed rigid skin layers $1_h$ which approximately correspond to the natural bone cortex or outer rind, whereas between the outer and inner rigid or hard skin layer of the wall 1 there appear microcellular rigid foam layers with closed cells of about 0.5 to 2.0 millimeters diameter. Such a wall structure remains solid up to temperatures of about 125° C, has a density of about 1000 g/liter and a compressive strength of about 800 to 1500 kg/cm².

As the core material for forming the inner cavity 10 there is advantageously employed an alloy having a low melting point (60° C to 95° C). Hence, the core insert is cast in conventional manner in a special mold. In so doing, it is advantageous to form at such core casting at least one axially protruding square of four-cornered plug which can be inserted into an appropriate recess or recesses of the outer mold parts and thus fixedly retain the mold core in the proper position. Such alignment plugs or pins 21 have been shown in phantom lines in FIG. 1 of the drawings and after the molding operation leave corresponding holes 58 in the socket head surfaces of the molded plastic bone 50. Depending upon requirements, such holes 58 can be filled with a hardened plastic paste. The injection channels for the infeed of the liquid reaction mixture into the mold produces the phantom line illustrated plugs 22 which can be cut off.

After the hardening or setting of the foamed reaction mixture the casting mold is heated to about 100° C in order to melt the core metal and to allow such to run-off.

A plastic bone constructed according to the showing of the drawings and the previous description, comprising a rigid polyurethane foam structure and an internal hollow cavity, with regard to its weight, its external shape and its internal shape, the machinability of its structure, especially the ability to insert screws and with regard to its strength and its rupture behavior, corresponds extensively to the natural structure. By scoring or scratching the outer skin or rind along preselectable rupture lines and/or weakening the wall strength along a particular inner groove 14 and application of appropriate bending- and/or torsion forces there can be simulated certain types of fractures. Also by applying blows to the bone there can be simulated complicated fragmentation or shattered bone fractures.

The surgeon who is to be trained in osteopathy will find the plastic bone heretofore disclosed to constitute an extremely valuable training device which can be used to experiment and prove the manual-mechanical techniques for joining together and threadably connecting and/or nailing bone fractures. Other types of human bones, preferably shaft bones with marrow cavity, can be manufactured according to the teachings of the invention without any difficulty.

In FIG. 1 of the drawings the wall of the proximal widened portion $10_p$ of the inner cavity 10 is weakened at the region below the tuberositas by means of an inner recess, in order at this location to facilitate the formation of a wall fracture for introducing a marrow nail and its driving elements.

While there are shown and described present preferred embodiments of the invention, it is to be distinctly understood that the invention is not limited thereto, but may be otherwise variously embodied and practiced within the scope of the following claims.

Accordingly, what is claimed is:

1. A plastic bone useful as a training device for surgeons for the mechanical joining of broken pieces of a bone fracture, comprising:
    a molded plastic bone having a size and shape essentially corresponding to a shaft bone of a limb of a human being;
    said molded plastic bone having an internal hollow cavity;
    said internal hollow cavity including a marrow cavity located at the central region of the molded plastic bone;
    said internal hollow cavity of the molded plastic bone being provided at said central region with a narrowmost substantially uniform and profiled cross-section having recesses extending between inwardly protruding ribs;
    said internal hollow cavity extending past the marrow cavity towards both ends of the molded plastic bone into the region of spongy structured bone lacunae (spongiosa) of the natural bone and widening at such locations to form widened portions;
    said molded plastic bone having a wall structure which essentially corresponds to the solid wall regions (compacta) of the natural structure as to weight, strength and mechanical machinability.

2. The plastic bone according to claim 1, wherein:
    the widened portions of the inner hollow cavity are filled at the region of the bone ends with a support material.

3. A plastic bone useful as a training device for surgeons for the mechanical joining of broken pieces of a bone fracture, comprising:
    a molded plastic bone having a size and shape essentially corresponding to a shaft bone of a limb of a human being;
    said molded plastic bone having an internal hollow cavity;
    said internal hollow cavity including a marrow cavity located at the central region of the molded plastic bone;
    said internal hollow cavity extending past the marrow cavity towards both ends of the molded plastic bone into the region of spongy structured bone lacunae (spongiosa) of the natural bone and widening at such locations to form widened portions;
    said molded plastic bone having a wall structure which essentially corresponds to the solid wall regions (compacta) of the natural structure as to weight, strength and mechanical machinability; and
    the molded plastic bone has a surrounding wall which at the region of at least one of the widened portions of the internal hollow cavity is reinforced by inwardly directed ribs.

4. The plastic bone as defined in claim 1, wherein:
    the wall of the widened portion defining a proximal end of the molded plastic bone of the internal hollow cavity is weakened at the region below the tuberositas.

* * * * *